United States Patent [19]
Hitzler et al.

[11] Patent Number: 5,894,001
[45] Date of Patent: Apr. 13, 1999

[54] FRAGRANCE VAPORIZER, IN PARTICULAR FOR TOILETS

[75] Inventors: Alfred Hitzler; Erich Harter, both of Mochenwangen, Germany

[73] Assignee: Venta Vertriebs AG, Huenenberg, Switzerland

[21] Appl. No.: 08/817,398

[22] PCT Filed: Oct. 14, 1995

[86] PCT No.: PCT/EP95/04042

§ 371 Date: Apr. 16, 1997

§ 102(e) Date: Apr. 16, 1997

[87] PCT Pub. No.: WO96/12143

PCT Pub. Date: Apr. 25, 1996

[30] Foreign Application Priority Data

| Oct. 17, 1994 | [DE] | Germany | 44 37 019 |
| Nov. 5, 1994 | [DE] | Germany | 44 39 555 |
| Nov. 18, 1994 | [DE] | Germany | 44 41 105 |

[51] Int. Cl.$^6$ ........................................ B01F 3/04
[52] U.S. Cl. ................ 261/92; 96/222; 96/283; 261/30; 261/DIG. 17
[58] Field of Search ............ 261/30, 92, DIG. 17, 261/DIG. 65; 96/222, 269, 283; 422/123, 124

[56] References Cited

U.S. PATENT DOCUMENTS

| 2,190,972 | 2/1940 | Boldt . | |
| 2,539,059 | 1/1951 | Cohn . | |
| 3,309,021 | 3/1967 | Powers | 261/92 |
| 3,465,605 | 9/1969 | Hylan . | |
| 3,598,370 | 8/1971 | Hoag | 261/92 |
| 3,834,680 | 9/1974 | Yost et al. | 261/92 |
| 3,880,124 | 4/1975 | Stratton | 261/92 |
| 3,948,627 | 4/1976 | Schwarz et al. | 261/92 |
| 4,261,930 | 4/1981 | Walker . | |
| 5,292,479 | 3/1994 | Haraga et al. | 422/124 |

FOREIGN PATENT DOCUMENTS

| 0118811 | 1/1988 | European Pat. Off. . |
| 1191751 | 10/1959 | France . |
| 2097434 | 3/1972 | France . |
| 2595839 | 9/1987 | France . |
| 6811039 | 5/1969 | Germany . |
| 7215456 | 7/1973 | Germany . |
| 2338744 | 2/1975 | Germany . |
| 2424140 | 8/1975 | Germany . |
| 7826361U1 | 3/1979 | Germany . |
| 7904003U1 | 6/1979 | Germany . |
| 7913695U1 | 8/1979 | Germany . |
| 3105379 | 9/1982 | Germany . |
| 3412745 | 8/1985 | Germany . |
| 4011514 | 12/1991 | Germany . |
| 666737 | 8/1988 | Switzerland . |
| 1598372 | 9/1981 | United Kingdom . |
| 90/02231 | 3/1990 | WIPO . |

*Primary Examiner*—C. Scott Bushey
*Attorney, Agent, or Firm*—Venable; Venable George H. Spencer; Catherine M. Voorhees

[57] ABSTRACT

A fragrance evaporator allows doses of fragrance to be released into the atmosphere in a controllable manner and only when required. The fragrance evaporator has a solid surface that may be wetted as required with liquid fragrance from a fragrance reservoir. An evaporation space that surrounds the solid surface and that is in communication with the atmosphere is thus created above the surface.

23 Claims, 6 Drawing Sheets

FRAGRANCE VAPORIZER, IN PARTICULAR FOR TOILETS

BACKGROUND OF THE INVENTION

The invention relates to a fragrance vaporizer, in particular for toilets having a liquid aromatic compound to be distributed within the air in a room.

In order to avoid or suppress unpleasant odors, for example in toilet facilities of restaurants, other public buildings, or even in buildings for private use, spraying agents have previously often been used. These nebulize a liquid aromatic compound in fine droplets in the air in the room. Some of these droplets vaporize almost completely and are thus located in the air in the room, which thus has the fragrance of this aromatic compound.

Usually, however, the sprayed aromatic compound does not vaporize completely. Some of the nebulized droplets settle on the floor, the walls, on fittings and on the clothing of people present in the room. This leads to unpleasant side effects. For instance, the floor may possibly become slippery, or clothing and shoes are attacked by the sometimes aggressive aromatic compounds, for example of ethereal oils. Because of this, the floor in public toilet facilities has to be wiped regularly at intervals of about 2 hours.

Furthermore, so-called odor blocks to avoid unpleasant odors have been disclosed. Odor blocks of this type have the disadvantage that they constantly give off their scent to the surrounding air in the room. This leads to waste of the aromatic compound since this is given off into the air in the room even when it is not necessary to combat a foreign odor, for example when the toilet is not being used. In the case of odor blocks, this deficiency also cannot be readily eliminated since it is not possible to regulate the dispensing of the aromatic compound in odor blocks.

SUMMARY OF THE INVENTION

The object of the invention is therefore to propose a fragrance vaporizer in which the aromatic compound can be regulated and can be fed to the air in the room only when required and in a meterable quantity.

Starting from a fragrance vaporizer of the type mentioned in the introduction, this object is achieved by a fixed surface which extends partially into a liquid aromatic compound and serves as a wettable surface and a vaporization chamber which surrounds the fixed surface wherein ambient air moves past the fixed surface and communicates with air in a room.

Advantageous designs and further developments of the invention are possible by means of the measures mentioned in the following description.

Accordingly, a fragrance vaporizer according to the invention has a fixed surface which can be wetted, when required, with a liquid aromatic compound from an aromatic-compound reservoir. In this case, a vaporization chamber which surrounds the fixed surface communicates with the air in the room.

Increased vaporization takes place due to the distribution of the liquid aromatic compound on the fixed surface. Since the vaporization chamber surrounding the fixed surface communicates with the air in the room, the desired fragrance effect can thus be brought about by introducing air enriched with aromatic compound from the vaporization space of the fragrance vaporizer into the room exposed to the odour. The fixed surface is only wetted with liquid aromatic compound when required, so that no unnecessary aromatic compound is distributed into the air in the room. The floor, walls, fittings or even clothing of a person present in the room are not wetted by aromatic compound. Since an aromatic-compound reservoir is provided, a sufficient quantity of aromatic compound is also available over a prolonged period.

The surface is advantageously arranged to be movable so that it can be immersed at least partially into an aromatic-compound bath for wetting with aromatic compound, and that the surface wetted by immersion can be moved after immersion out of the aromatic-compound bath into the vaporization chamber.

In this way, at least the immersed part of the surface is completely wetted with the aromatic compound.

Any remaining residue of aromatic -compound on the surface prior to immersion does not cause any harm in this case, but is fed back to the aromatic-compound reservoir during immersion. After moving the wetted surface into the vaporization chamber, the vaporization of the aromatic compound can then take place.

A stack of discs is advantageously provided, in which there is an open gap between the individual discs, the surface of the discs forming the surface to be wetted for the liquid aromatic compound. Such a lamellar arrangement of discs in a stack results in a very large wetted surface when the stack of discs is immersed in the aromatic-compound bath with a comparatively small outside dimension. Owing to this large surface, increased vaporization of aromatic compound occurs as soon as the wetted part of the stack of discs is introduced into the vaporization chamber.

In a preferred embodiment, the stack of discs is configured to be cylindrical and rotatable. A stack of discs designed in this way lies with its axis of rotation parallel to the liquid surface of the aromatic-compound bath, so that part of the surface of the stack of discs is constantly located in the aromatic-compound bath, while another, wetted part of the surface of the stack of discs constantly passes through the vaporization chamber during the rotational movement. As a result, a continuous and complete wetting of the surface of the stack of discs is reliably guaranteed.

An impeller is preferably provided as a fan to ventilate the vaporization chamber. By means of the fan and the conduction, thus caused, of the air enriched with aromatic compound out of the fragrance vaporizer and the constant flow of fresh air over the wetted surface in the vaporization chamber, an intensification of the vaporization operation is achieved. The vaporization chamber and its corresponding openings can thus be designed to be of a relatively compact size, thus having a positive effect on the overall construction size of the fragrance vaporizer.

It is recommended to provide the same motor for driving the stack of discs and the fan, since this will save the cost of a second drive motor for the stack of discs or for the fan.

A fragrance vaporizer according to the invention is advantageously not used in continuous operation. In contrast, it is recommended to provide a control for the fragrance vaporizer, which control permits intermittent operation, i.e. a mode of operation with interim stoppage. As a result, the saving effect which is possible in respect of the quantity of aromatic compound required compared to a fragrance vaporizer with continuous vaporization is fully utilized. In addition, the electricity consumption is also reduced as a result, so that, in the case of battery or accumulator operation, the electricity supply is maintained over a prolonged period without exchanging the battery or recharging an accumulator.

In an advantageous design of the invention, a control is provided in which the operating times of the vaporizer can be controlled by a wide variety of sensors and/or by one or more time intervals. Possible sensors in this case are the door switch of the entrance door to the room, the light switch of the room or a light sensor operating independently thereof, a sensor which reacts to the water flushing, for example a pressure switch in a toilet, or a sensor which registers the removal of toilet paper. In particular, the use of an odor sensor is of great advantage. As a result, the operating time of the fragrance vaporizer can be optimized in terms of a good result in regenerating the air in the room. Other sensors which may possibly comprise simple switches can also be used as a control of a fragrance vaporizer according to the invention.

Various modes of operation are possible with the aid of time intervals. For instance, using an after-running control in which the device is switched on manually by a button, the fragrance vaporizer can continue running for a specific time, for example between 30 and 150 seconds after each switching-on operation, and can then switch off automatically.

Depending on the field of use, the device can also be controlled to intermittent operation between a specific period of running time and a specific pause time. As an example, a switch setting in which the running time is 45 seconds and the pause time is 25 minutes would be conceivable. In such a mode of operation, the air in the room is freshened at regular intervals following the pause times. In this case, the running time and the pause time depend on the size of the room and the intensity of the odor pollution.

The control can also be switchable between different modes of operation. Thus, for example, a control may be provided with a mode of operation with the abovementioned intervals of 45 seconds running time and 25 minutes pause time and with a further mode of operation of, for example, 120 seconds running time and 25 minutes pause time. The modes of operation can run for a specific predetermined time or even run continuously automatically until either the mode of operation is changed or the control is moved into a switch setting in which the fragrance vaporizer is stopped.

The intermittent mode of operation with intervals can be combined with an after-running control so that, after the fragrance vaporizer has been switched on manually, the control is in an intermittent state of operation for a specific period. It can also be coupled to a sensor, so that the switching-on and switching-off are controlled with the aid of the sensor signals, and the intermittent mode of operation runs between these points in time.

In the simplest embodiment, it is also possible for the fragrance vaporizer according to the invention to be actuable in a purely manual manner.

A fragrance vaporizer according to the invention is preferably provided with at least one exchangeable cartridge for the aromatic-compound bath. Various scents can thus easily be used with a fragrance vaporizer for air regeneration. The scents can thus be exchanged in a simple and clean manner, as a result of which a fragrance vaporizer according to the invention can also be used, for example, for use in so-called aromatherapy.

The exchangeable cartridge for the aromatic-compound bath is preferably designed to be exchangeable as a complete unit together with the stack of discs, which is wetted with the aromatic compound of the respective scent, and is provided with a lid. Consequently, mixing of aromatic compound of different scents is virtually completely ruled out. Aromatic compounds of different scents do not come into contact with one another through the exchange of the exchangeable cartridge. By closing the exchangeable cartridge with a tightly closing cap, such an exchangeable cartridge can be transported without difficulty or can also be stored over a prolonged period. During storage over a prolonged period, there would otherwise be the risk of an open exchangeable cartridge drying out or, if the aromatic compound is introduced into a liquid carrier medium, the risk of "scent off-loading", i.e. the loss of the aromatic compound within the carrier medium.

In further embodiments of the invention, two or more stacks of discs are used. As a result, virtually any outside dimensions of a fragrance vaporizer according to the invention can be realized without detracting from its efficiency.

In the case of the drive of rollers, shafts or the like, in particular also in the case of the drive of a stack of discs of a vaporizer according to the invention, which rotate within a liquid, problems occur over and again due to the transmission becoming contaminated by the corresponding liquid.

This is disadvantageous, in particular, when the liquids concerned are aggressive. In the case of a present fragrance vaporizer, such liquids are present, for example, in the form of ethereal oils. However, this is also a general problem, for example, in the chemical sector, where aggressive liquids, in particular acids -and alkalis, are frequently handled.

Comprehensive sealing measures of the transmission unit do not always lead to the desired success. The only possible solution often remaining is to produce all the transmission components from materials which are resistant to the aggressive liquids used.

In general, this involves increased cost expenditure, in which case the problem still remains that the transmission unit is contaminated by the respective liquid used.

In particular when changing the liquid, i.e. in the case of a present fragrance vaporizer when changing the aromatic-compound bath, undesirable mixing of liquids may occur. In this case, undesirable chemical reactions may even occur, specifically in chemical production plants, if the transmission is not cleaned with the utmost care.

In a fragrance vaporizer according to the invention, it is therefore recommended, and also generally in any field of application in which an object, such as a roller, shaft or the like, in a present fragrance vaporizer, for example, the stack of discs, rotates in an aggressive liquid, to provide a drive which comprises at least one lever and one gearwheel, the gearwheel being connected to the rotating object so as to be secure against rotation. Moreover, a device is provided for mounting and guiding the lever for a forward movement of the lever which engages in the gearwheel and carries it along.

Even if, in this case, the gearwheel is wetted by the liquid due to the rotational movement in the said liquid, the only point of contact with the other transmission components is in that part of the lever which engages in the gearwheel. This part of the lever, however, is generally easy to clean. Moreover, the movement of the lever can be guided and controlled in such a way that, for the case of it actually coming into contact with the liquid, these residues of liquid drain away in the direction of the lever tip and consequently in fact only an extreme end of the lever is wetted by the liquid.

For this purpose, the lever is preferably oriented and configured in such a way that it engages in the gearwheel with its tip pointing towards the gearwheel and that the said tip is aligned downwards in any position of the lever.

The device for mounting and guiding the lever is advantageously set up in such a way that it permits a reverse movement which takes place between two forward movements of the lever and during which the lever is no longer in engagement with the gearwheel and does not touch the latter.

Consequently, the lever can drive the gearwheel continuously in one direction of rotation. In addition, a pawl drive can, inter alia, be dispensed with as a result, which drive, in the manner of a ratchet, slides during the reverse movement with its pawl over the teeth of the gearwheel, the pawl engaging in the gearwheel during the forward movement. In this case, on the one hand a movable component which is required additionally for a pawl drive is dispensed with and, on the other hand, the development of noise of a pawl drive which is actually very annoying in living rooms is avoided completely.

The device for mounting and guiding the lever preferably comprises slide surfaces which are mounted on the lever itself and a fastener with guide surfaces. As a result, the lever can, apart from a pivoting movement, also carry out a translatory movement which is superimposed on the pivoting movement. By means of the superimposition of a rotational and a translatory movement, it is possible to actuate the tip in such a way that it engages in the gearwheel during the forward movement and is disconnected therefrom during the reverse movement.

The lever is advantageously connected at one end in an eccentrically articulated manner to a rotating drive shaft. By means of such an eccentrically articulated connection to a rotating shaft, the lever is simultaneously set in a pivoting and translatory movement, which movements are superimposed on one another. In conjunction with the slide and guide surfaces, in this case virtually any desired cyclical movement, for example an elliptical movement, of the lever tip can be brought about. For this purpose, the shapes of the slide and guide surfaces and the eccentricity of the lever drive must be matched with one another.

In a drive according to the invention, two levers are preferably provided, which engage alternately in the gearwheel. There is thus constantly one lever in engagement with the gearwheel, so that the latter is not only driven, but is also locked against any undesirable further movement, for example against the rotating object turning back after a lever tip has been pivoted out of the gearwheel. The rotation of the rotating object is thus constantly monitored and controlled mechanically securely by the lever drive.

The two levers are preferably eccentrically linked to the same drive shaft offset at 180°. If both levers have slide surfaces of the same shape and slide in corresponding guide surfaces, they correspondingly execute identical forward and reverse movements which are carried out temporally offset relative to one another by half a cycle length.

In a preferred embodiment, the drive shaft for the eccentric drive of the lever is fitted with a worm wheel in which a worm engages. As a result, on the one hand extreme transmission ratios are possible, which is necessary, in particular when used in a fragrance vaporizer according to the invention, where a motor is used for the fan and for the rotation of the stack of discs. On the other hand, a worm wheel drive constitutes a so-called self-inhibiting transmission, which results, in conjunction with the two-lever system in which one lever is constantly in engagement with the gearwheel of the rotating object, in locking of the rotating object, for example a stack of discs, when the drive is switched off.

The worm is preferably connected via an elastic coupling to the drive shaft of a motor. As a result, the drive shaft does not need to be completely precisely in alignment with the shaft of the worm. Relatively large tolerances in the production of a drive according to the invention are possible in this case, which, inter alia, results in saving costs.

BRIEF DESCRIPTION OF THE DRAWINGS

An exemplary embodiment of the invention is explained in greater detail with reference to the following description and illustrated in the drawings in which:

FIG. 3 shows a diagrammatic cross-section through an exchangeable cartridge with a closing cap fitted on;

DETAILED DESCRIPTION OF THE INVENTION

Figure 1:
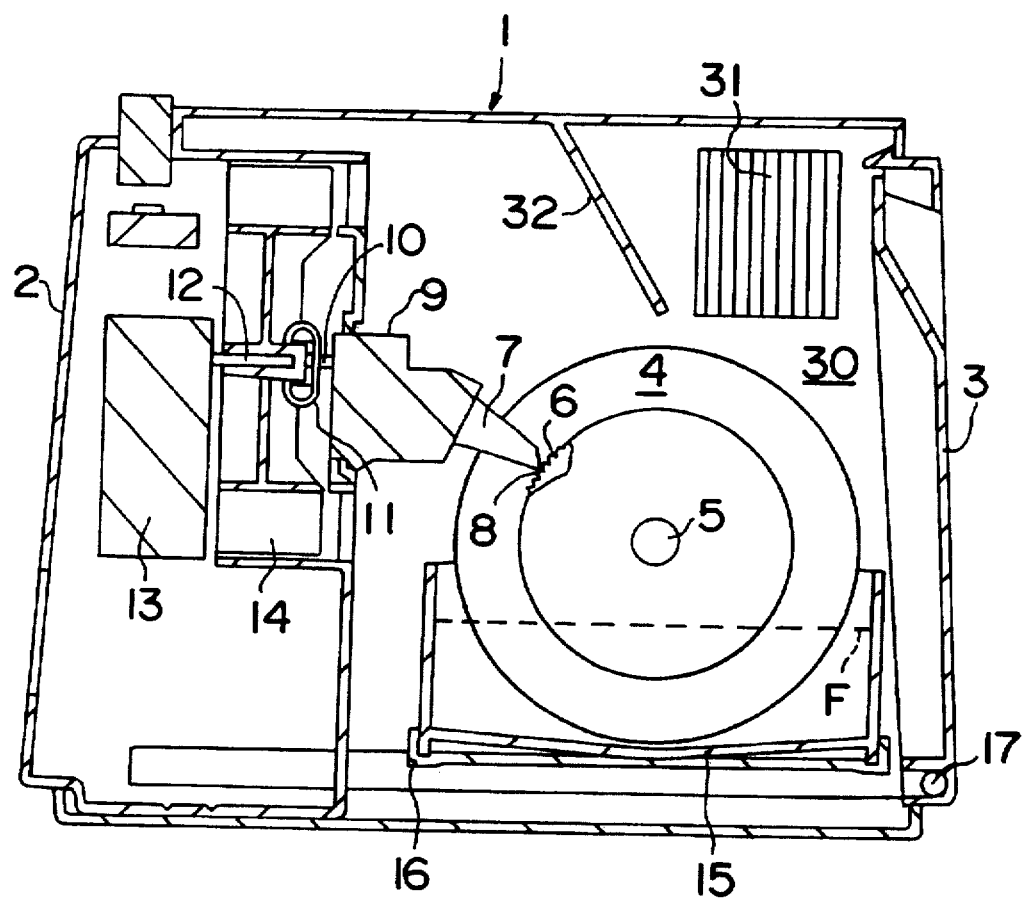
FIG. 1 shows a diagrammatic cross-section through a fragrance vaporizer according to the invention.

The fragrance vaporizer 1 according to FIG. 1 has a housing 2 with an opening flap 3. Illustrated inside the housing 2 is a stack of discs 4 consisting of circular discs arranged one behind the other in a lamellar manner. In the illustration shown, in this case only the front disc is visible. A gear or gearwheel 6 is firmly connected to the spindle 5 of the stack of discs 4. A lever 7 engages with its lever tip 8 in the gearwheel 6. The rear end of the lever 7 is hidden in a transmission housing 9. Passing through the transmission housing 9 is a transmission drive shaft 10 which is connected via an elastic coupling 11 to a motor drive shaft 12 of an electric motor 13. An impeller 14 is fitted as a fan on the motor drive shaft 12.

The stack of discs 4 is mounted so as to be rotatable with its spindle 5 in the end faces (not illustrated) of an aromatic-compound trough 15. The aromatic-compound trough 15 stands in a displaceable drawer fastener 16 to which the opening flap 3 is also attached pivotably at its axis of rotation 17 (not illustrated in detail).

Figure 3:
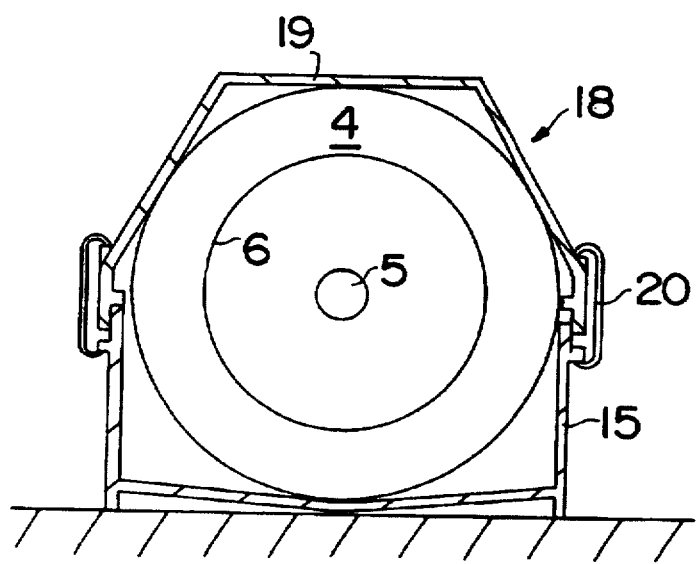

FIG. 3 illustrates a complete exchangeable cartridge 18 for the aromatic-compound bath. It comprises the aromatic-compound trough 15 with the stack of discs 4 mounted therein and a cartridge cap 19 which is attached on the aromatic-compound trough 15 by means of closure clips 20.

Figure 4:
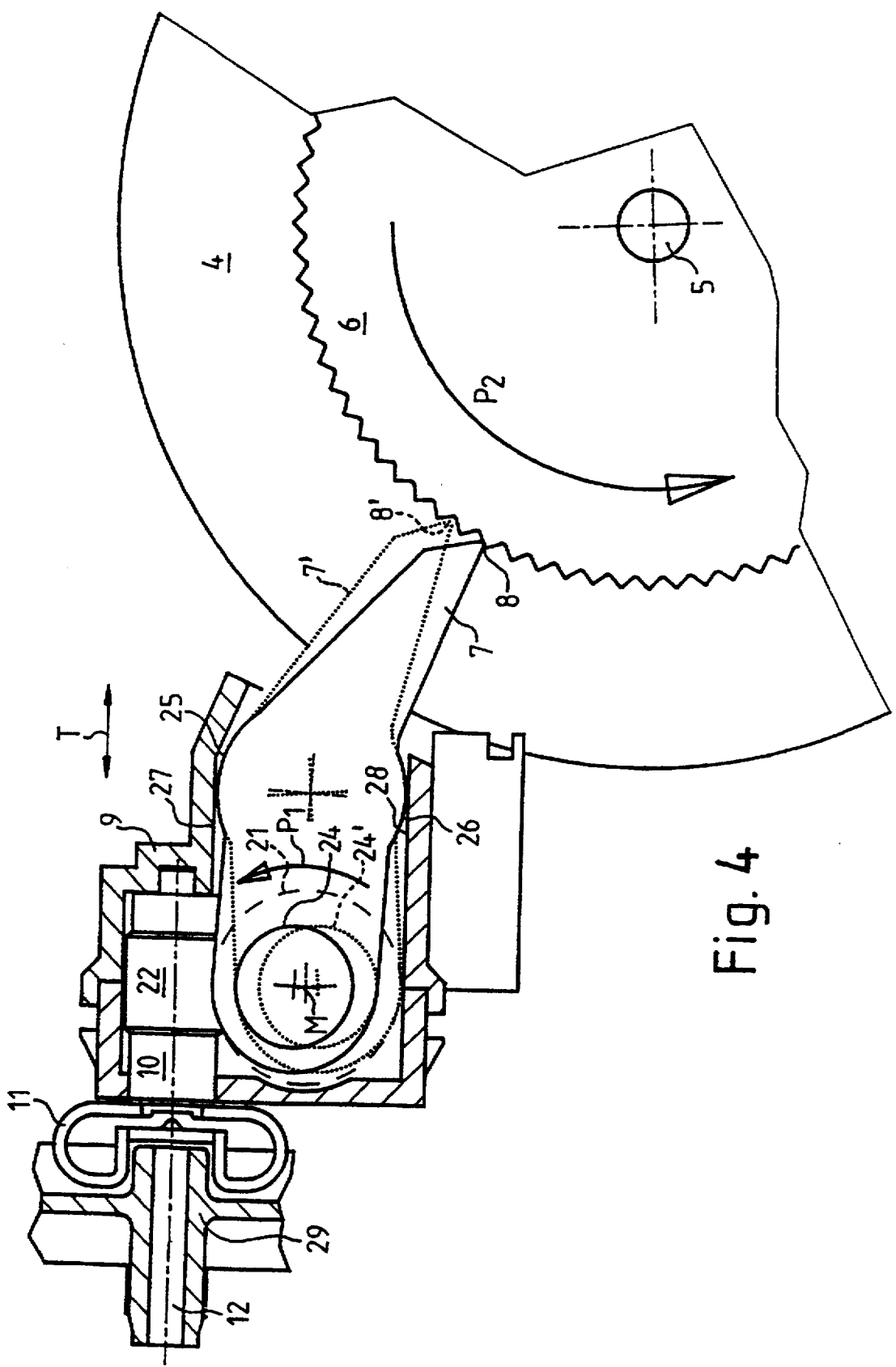
FIGS. 4 and 5 show a diagrammatic cross-section through a drive system according to the invention in various lever positions.
Figure 5:
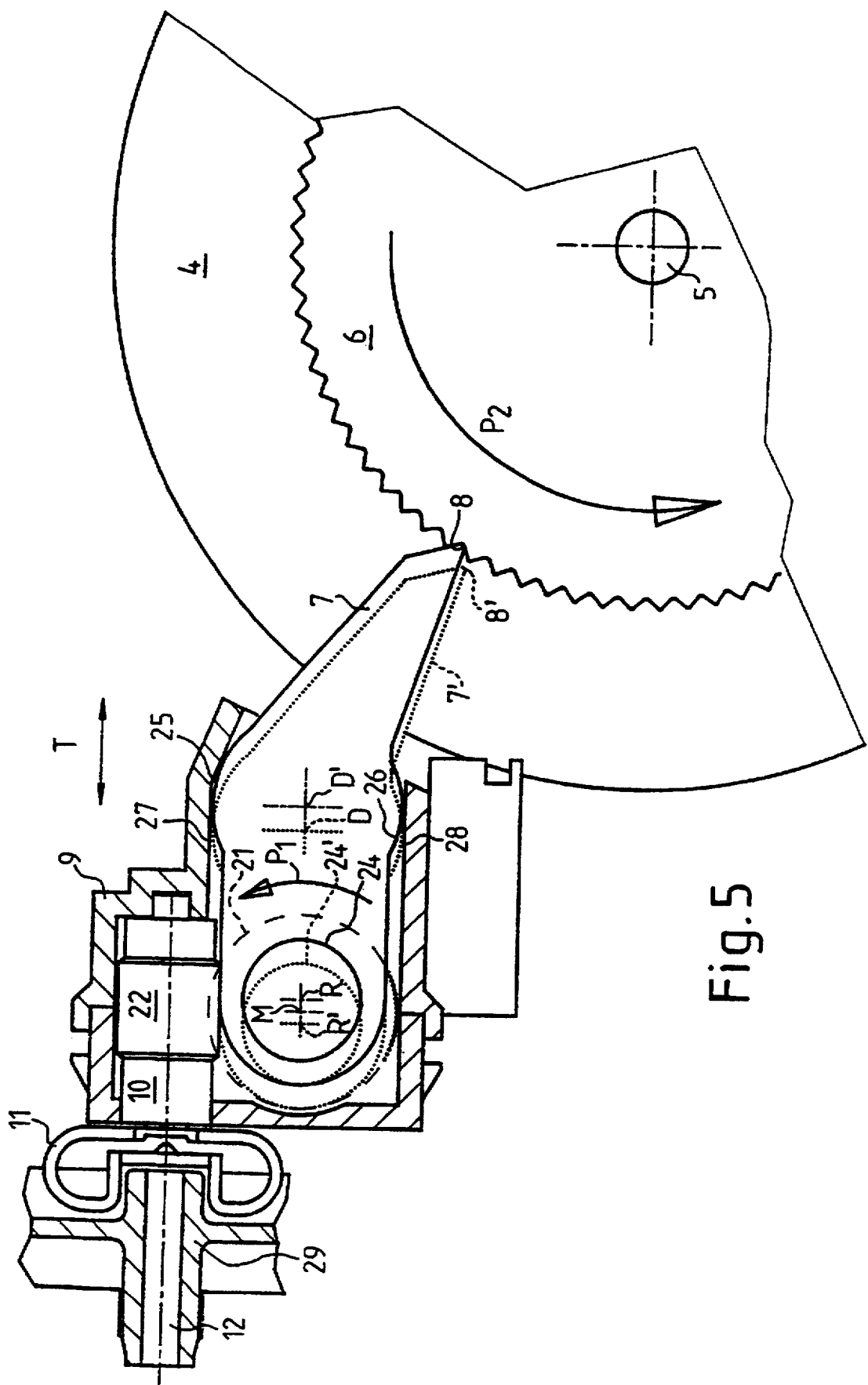

FIGS. 4 and 5 show an enlarged illustration of a lever drive according to the invention. In this case, a front lever 7 is illustrated by solid lines, while a second lever 7' located behind the lever 7 is marked by dotted lines.

A worm wheel 21 which meshes with a worm 22 is shown by dashed lines. The worm wheel 21 is connected securely against rotation to an eccentric drive shaft 23, or is recessed into the latter, which is not illustrated in detail in FIGS. 4 and 5 but can be seen from FIG. 6. Seated on the eccentric drive shaft 23 are two eccentrics 24, 24' which are configured as annular shoulders and whose mid-axes R, R' are offset relative to the mid-axis M of the eccentric drive shaft 23, thus resulting in eccentricity. The eccentrics 24, 24' pass through two corresponding bores in the respective lever 7, 7'. Each lever 7 or 7' is provided in each case with an upper 25 and a lower 26 slide surface. These slide surfaces lie on upper 27 and lower 28 guide surfaces which are recessed into the transmission housing 9.

Figure 6:
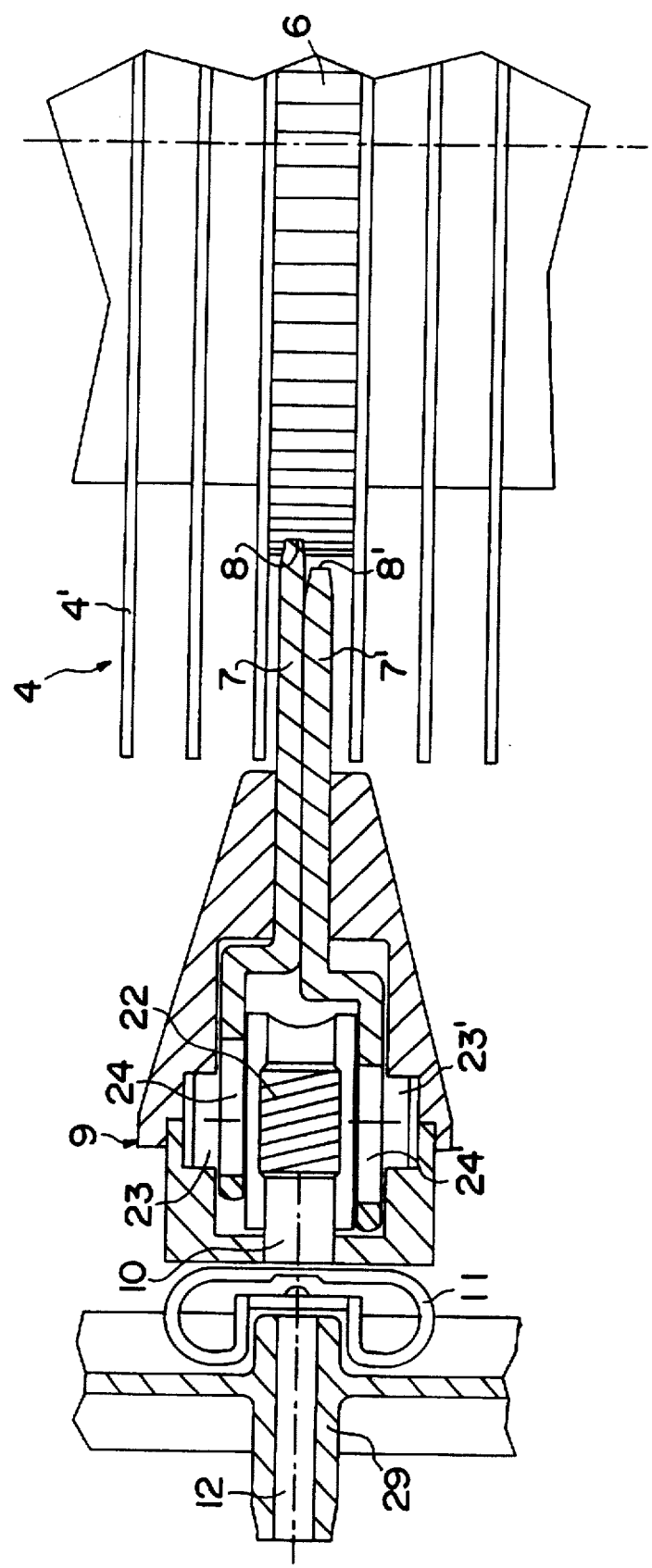
FIG. 6 shows a diagrammatic vertical cross-section through a part of the drive device.

FIG. 6 shows the worm 22 which is connected securely against rotation to the transmission drive shaft 10 or is recessed into the latter. The elastic coupling 11 is connected to the motor drive shaft 12 via a bush 29 of the impeller 14. Moreover, the lamellar arrangement of the individual discs 4' of the stack of discs 4 can be seen here.

During operation of the fragrance vaporizer 1 according to the invention, there is a liquid aromatic compound in the aromatic-compound trough 15, as illustrated by the line F as the liquid level. A stack of discs 4 lies partly within the aromatic compound. The said stack of discs is mounted via its spindle 5 so as to be rotatable in the aromatic-compound trough 15. It is set in a rotational movement via the levers 7, 7' and the gearwheel 6. In this case, the surface of the stack of discs 4 wetted with aromatic compound comes into contact with the air in the vaporization chamber 30 so that the aromatic compound vaporizes from the surface into the air in the vaporization chamber 30.

By means of the impeller 14, air is sucked in via an opening (not illustrated in detail) in the housing 2 of the fragrance vaporizer 1 and is blown over the stack of discs 4. This results in an intensified vaporization of aromatic compound. The air enriched with aromatic compound in the vaporization chamber 30 subsequently escapes through corresponding ventilation openings, as are indicated diagrammatically by the ventilation slots 31. In this case, a screen 32 additionally deflects the air flow in the direction of the stack of discs.

Figure 2:
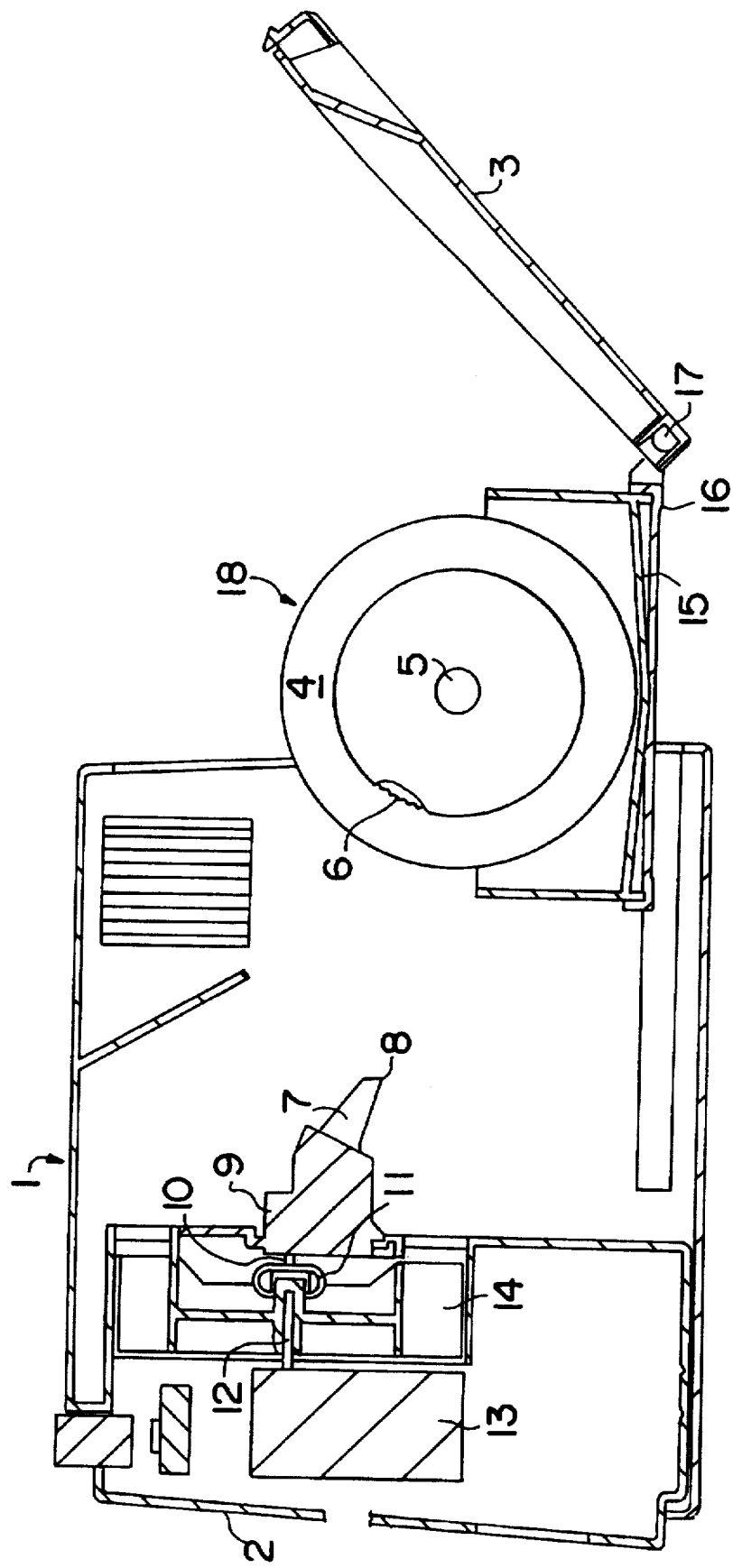
FIG. 2 shows a cross-section according to FIG. 1 while an exchangeable cartridge is being removed.

If the aromatic compound is to be changed, the flap 3 can be folded down, as illustrated in FIG. 2, and the aromatic-compound trough 15 can be pulled out on the drawer fastener 16. In this case, the stack of discs 4 remains mounted in the aromatic-compound trough 15. The exchangeable cartridge 18 which comprises the aromatic-compound trough 15 together with its stack of discs 4, can subsequently be removed from the drawer fastener 16 and closed with a cartridge cap 19. This exchangeable cartridge 18 is thus ready for prolonged storage or for transportation. Another exchangeable cartridge of identical design or even the same exchangeable cartridge 18 can subsequently be inserted into the fragrance vaporizer 1 again in the reversed order.

The stack of discs 4 is driven by the gearwheel 6 and the levers 7, 7'. The levers 7, 7' are driven with the aid of the electric motor 13 which also drives the impeller 14. This takes place via the bush 29 of the impeller 14 and the elastic coupling 11, as a result of which the transmission drive shaft 10 is driven.

As a result, the worm 22 and thus also the eccentric drive shaft 23 rotate in the direction of the arrow $P_1$. In this case, the eccentrics 24 execute a circular movement. By means of this circular movement, the levers 7, 7' are set both in a tilting movement about the pivot D, D' and in a translatory movement in the direction of the double arrow T. During these movements, each lever is guided by the upper and lower guide surface 27, 28 on which it lies with its upper and lower slide surfaces 25, 26. By means of the special shaping of the guide surfaces 27, 28 and of the slide surfaces 25, 26 in conjunction with the deflection of the mid-axes R, R' of the eccentrics 24, 24' from the mid-axis M of the axis of rotation 23, virtually any desired curved path of the lever tips 8, 8' is possible. In this case, an elliptical curved path is of great advantage, so that the lever tips 8, 8' are in engagement with the gearwheel 6 during the forward movement, i.e. during the downward movement in the present illustration. During the reverse movement, i.e. in this case during the upward movement, the lever tips 8, 8' are then out of engagement with the gearwheel 6 and do not touch its teeth.

The illustrations of FIGS. 4–5 show the levers 7, 7' in different positions during the drive operation, in which the stack of discs 4 is rotated in the direction of the arrow $P_2$. Since the deflection of the eccentrics 24, 24' relative to the mid-axis M of the eccentric drive shaft 23 lies offset relative to one another by 180°, i.e. the mid-axes R, R' of the eccentrics 24, 24' and the mid-axis M of the eccentric drive shaft 23 lie on a straight line, the movement of the lever 7' is completed offset by half a movement cycle relative to the movement of the lever 7. As a result, at least one lever tip 8 is in engagement in each case with the gearwheel 6, so that the latter is not only carried along in the direction $P_2$, but is also locked in any position of the drive in relation to other movements, for example turning back counter to the direction of rotation of $P_2$.

The lever tips 8, 8' are directed downwards so that liquid which is possibly conveyed to the lever tips 8, 8' due to the immersion of the gearwheel 6 in the aromatic compound inside the aromatic-compound trough 15 drains off again down to the gearwheel 6. The only locations which can thus come into contact with aromatic compound are only the tips of the levers 7, 7'. There is thus no risk of the remaining components of the drive coming into contact with liquid aromatic compound in any phase of the operation of the fragrance vaporizer.

The illustrated drive for the stack of discs 4 can also be used outside a fragrance vaporizer according to the invention. The system illustrated can readily be applied on any rotating object, even in the design according to FIG. 7 described below, in which a drive system according to the invention is advantageous. This may be the case, in particular, in chemical production plants where rollers, shafts or the like likewise often have to rotate within a liquid bath, and the problem thus likewise occurs that the drive must not come into contact, or only at some points, with the possibly aggressive liquid.

Figure 7:
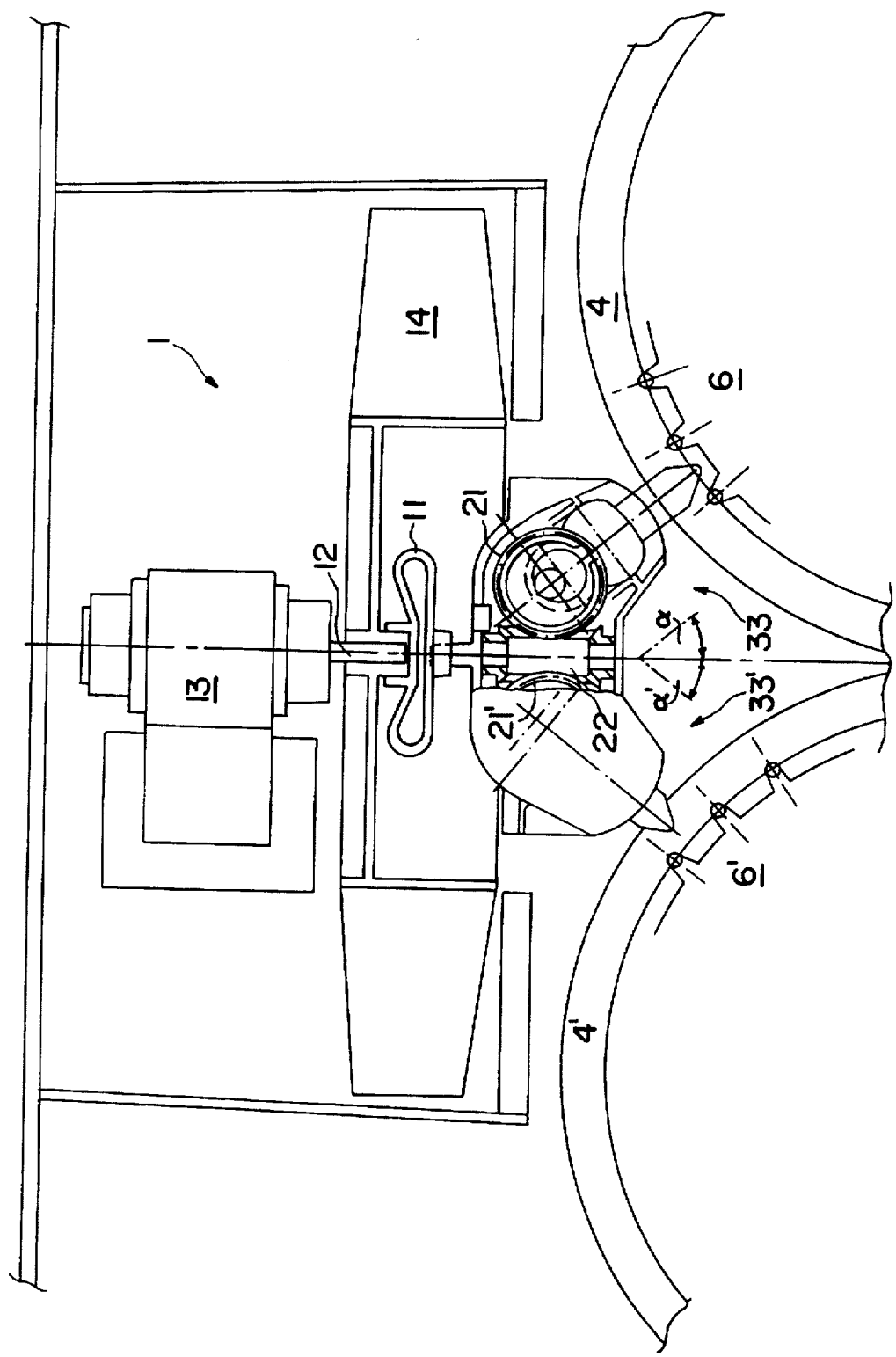
FIG. 7 shows a diagrammatic illustration of a fragrance vaporizer with two stacks of discs and a double drive.

FIG. 7 illustrates a further embodiment of a fragrance vaporizer according to the invention. In this case, two stacks of discs 4, 4' each with a gearwheel 6, 6' are disposed parallel to one another. They are driven by means of a double lever drive 33, 33'. The lever drives 33 correspond to the previous simple lever drives described above. They are driven by means of a common worm 22 and the two worm wheels 21, 21'. In the present case, the axis of the worm 22 and thus also of the transmission drive shaft 10 is arranged vertically, the two lever drives 33, 33' being disposed obliquely at an angle α or α' relative to the vertical axis of the transmission drive shaft. Correspondingly, the impeller 14 and the electric motor are also arranged with a vertically extending axis.

By using two parallel stacks of discs, the wetted surface is enlarged overall, only one drive motor and one fan still being necessary as before. Owing to the said spatial arrangement of the stacks of discs, a compact construction is possible with high efficiency of a fragrance vaporizer according to the invention.

We claim:

1. A fragrance vaporizer for toilets comprising:

a housing;

a liquid aromatic compound to be distributed within ambient air in a room;

a rotating stack of discs which extends partially into an aromatic-compound reservoir provided with the liquid aromatic compound and which serves as a wettable surface;

a lever drive for rotating the stack of discs; and a fan for moving the ambient air past the wetted surface;

wherein the aromatic-compound reservoir is a separate aromatic-compound trough which can be removed from the housing and into which the stack of discs is inserted.

2. A fragrance vaporizer according to claim 1, wherein an impeller is provided as the fan for ventilation of the vaporization chamber formed in the housing.

3. A fragrance vaporizer according to claim 2, further comprising a motor for driving both the stack of discs and the impeller.

4. A fragrance vaporizer according to claim 1, further comprising a control which permits intermittent operation of the rotating stack.

5. A fragrance vaporizer according to claim 1, further comprising a control of the drive in which the operating time of the fragrance vaporizer can be controlled by one of sensors and one or more time intervals.

6. A fragrance vaporizer according to claim 1, wherein at least one exchangeable cartridge is provided for the aromatic-compound bath.

7. A fragrance vaporizer according to claim 1, wherein at least two stacks of discs are provided.

8. A fragrance vaporizer according to claim 1, wherein the drive for the rotating stack of discs further comprises at least one pivotably mounted lever and a gearwheel, the gearwheel being connected securely against rotation to the rotating stack of discs, and a device for mounting and guiding the lever being present for a forward movement of the lever which engages in the gearwheel and carries it along.

9. A fragrance vaporizer according to claim 8, wherein the lever engages in the gearwheel with its tip pointing towards the gearwheel, and said tip of the lever is aligned downwards in any position of the lever.

10. A fragrance vaporizer according to claim 8, wherein the device for mounting and guiding the lever is set up for a reverse movement which takes place between two forward movements of the lever and during which the lever is no longer in engagement with the gearwheel and does not touch the gearwheel during the reverse movement.

11. A fragrance vaporizer according to claim 8, wherein the device for mounting and guiding the lever comprises slide surfaces on the lever and a fastener with guide surfaces.

12. A fragrance vaporizer according to claim 8, wherein the lever is connected at one end in an articulated manner to an eccentric drive shaft via an eccentric.

13. A fragrance vaporizer according to claim 8, wherein there are two levers.

14. A fragrance vaporizer according to claim 12, wherein the eccentric drive shaft for the lever is provided with a worm wheel in which a worm engages.

15. A fragrance vaporizer according to claim 14, wherein the worm is connected via an elastic coupling to a drive shaft of a motor.

16. An apparatus having a stack of rotating discs which extend partially into a liquid and which serve as a wettable surface, ambient air being moved past the stack by a ventilator, comprising at least one pivotably mounted lever and a gearwheel, said gearwheel being connected securely against rotation relative to the stack of discs, and a device for mounting and guiding said lever so that the lever engages said gearwheel and moves the gearwheel forward.

17. A drive according to claim 16, wherein said lever engages the gearwheel with its tip pointing towards the gearwheel and said tip of the lever is aligned downwards in any position of said lever.

18. A drive according to claim 16, wherein said device for mounting and guiding the lever is set up for a reverse movement which takes place between two forward movements of the lever and during which the lever is no longer in engagement with the gearwheel and does not touch the gearwheel during the reverse movement.

19. A drive according to claim 16, wherein said device for mounting and guiding the lever comprises a slide surface on the lever and a fastener with guide surfaces.

20. A drive according to claim 16, comprising two levers.

21. A drive according to claim 16, wherein said lever is connected at one end in an articulated manner to an eccentric drive shaft via an eccentric.

22. A drive according to claim 21, wherein said eccentric drive shaft for the lever is provided with a worm wheel in which a worm engages.

23. A drive according to claim 22, wherein said worm is connected via an elastic coupling to a drive shaft of a motor.

* * * * *